US005945336A

United States Patent [19]
Brown et al.

[11] Patent Number: 5,945,336
[45] Date of Patent: *Aug. 31, 1999

[54] OLIGONUCLEOTIDES AND METHODS FOR INHIBITING CELLULAR PROLIFERATION

[75] Inventors: Steven Joel Brown, La Jolla; Nanibhushan Dattagupta, San Diego, both of Calif.; Yathi M. Naidu, Park Ridge, Ill.

[73] Assignee: Gen-Probe Incorporated, San Diego, Calif.

[ * ] Notice: This patent is subject to a terminal disclaimer.

[21] Appl. No.: 08/975,570

[22] Filed: Nov. 21, 1997

Related U.S. Application Data

[63] Continuation of application No. 08/486,408, Jun. 7, 1995, Pat. No. 5,716,846.

[51] Int. Cl.$^6$ .............................. C07M 21/00; C12N 5/06

[52] U.S. Cl. .......................................... 435/375; 536/24.5
[58] Field of Search ................................ 435/6, 325, 375; 514/44; 536/24.31, 24.5; 935/8, 34, 36, 78

[56] References Cited

U.S. PATENT DOCUMENTS

| | | | |
|---|---|---|---|
| 5,225,326 | 7/1993 | Bresser et al. | 435/6 |
| 5,252,723 | 10/1993 | Bhatt | 536/25.3 |
| 5,470,824 | 11/1995 | Miles et al. | 514/2 |
| 5,489,519 | 2/1996 | Deeley et al. | 435/69.1 |
| 5,585,479 | 12/1996 | Hoke et al. | 536/24.5 |
| 5,716,846 | 2/1998 | Brown et al. | 435/375 |

FOREIGN PATENT DOCUMENTS

| | | |
|---|---|---|
| 9207864 | 5/1992 | WIPO . |
| 9425036 | 11/1994 | WIPO . |
| 9429444 | 12/1994 | WIPO . |
| 9503427 | 2/1995 | WIPO . |
| 9503788 | 2/1995 | WIPO . |

OTHER PUBLICATIONS

Antisense '97: A roundtable on the state of the industry . Nature Biotechnology 15: 519–524.
Bangham, et al. Diffusion of univalent ions across the lamellae of swollen phospholipids. *J. Med. Biol.* 13:238–252 (1965).
Caruthers, et al. Chemical synthesis of deoxyoligonucleotides by the phosphoramidite method. *Methods in Enzymology* 154:287–313 Academic Press Inc. (1987).
Girasole, et al. Estradiol inhibits interleukin–6 production by bone marrow–derived stromal cells and osteoblasts in vitro: a potential mechanism for the antiosteoporotic effect of estrogens. *The Journal of Clinical Investigation, Inc.* 89:883–891 (1992).
Grossman, et al. Interleukin 6 is expressed in high levels in psoriatic skin and stimulates proliferation of cultured human keratinocytes. *Proc. Natl. Acad. Sci.* 86:6367–6371 Medical Sciences (1989).

Hibi, et al. Molecular cloning and expression of an IL–6 signal transducer, gp130. *Cell* 63:1149–1157 Cell Press (1990).
Jilka, et al. Increased osteoclast development after estrogen loss: mediation by interleukin–6. *Science* 257:88–91 (1992).
Klein, et al. Interleukin–6 is the central tumor growth factor in vitro and in vivo in multiple myeloma. *Eur. Cytokine Net.*, 1:193–201 (1990).
Levy, et al. Interleukin–6 antisense oligonucleotides inhibit the growth of human myeloma cell lines. *J. Clin. Invest.* 88:696–699 The American Society for Clinical Investigation, Inc. (1991).
Majumdar, et al. Stepwise mechanism of HIV reverse transcriptase: primer function of phosphorothioate oligodeoxynucleotide. *Biochemistry* 28:1340–1346 American Chemical Society (1989).
Milligan, et al. Development of antisense therapeutics. Implications for cancer gene therapy. *Annals New York Academy of Sciences* 716:228–241 (1994).
Scala, et al. Expression of an exogenous interleukin 6 gene in human epstein barr virus B cells confers growth advantage and in vivo tumorigencity. *J. Exp. Med.* 172:61–68 The Rockefeller University Press (1990).
Shuin, et al. The activity of topoisomerases is related to the grade and stage in human renal cell carcinoma. Anticancer Research 14(6B), 2621–2626 (1994.
Stec, et al. Automated solid–phase synthesis, separation, and stereochemistry of phosphorothioate analogues of oligodeoxyribonucleotides. *J. Am. Chem. Soc.* 106:6077–6079 American Chemical Society (1984).
Stein, et al. Phosphorothioate oligodeoxynucleotides–anti–sense inhibitors of gene expression. Pharmac. Ther. 52:365–384 Pergamon Press Ltd. Great Britain (1992).
Taga, et al. Receptors for B cell stimulatory factor 2 quantiation, specificity, distribution, and regulation of their expression. *J. Exp. Med.* 166:967–981 The Rockefeller University Press (1987).
Taga, et al. Interleukin–6 triggers the association of its receptor with a possible signal transducer, gp130. *Cell* 58:573–581 Cell Press (1989).
Takenawa, et al. Enhanced expression of interleukin–6 in primary human renal cell carcinomas. *Journal of the National Cancer Institute* 83:1668–1672 (1991).

(List continued on next page.)

*Primary Examiner*—George C. Elliot
*Assistant Examiner*—Thomas G. Larson
*Attorney, Agent, or Firm*—Charles B. Cappellari

[57] ABSTRACT

The present invention relates to methods of treating disease-associated cellular proliferation using oligonucleotides. In particular, it relates to the use of oligonulceotides which are substantially complementary to interleukin-6 receptor mRNA sequences. In the form of pharmaceutical compositions, these oligonucleotides are suitable for administration to human subjects for the treatment of abnormal cellular proliferation due to such diseases as cancer, autoimmune disorders and viral infection.

44 Claims, No Drawings

OTHER PUBLICATIONS

Vink, et al. Mouse plasmacytoma growth in vivo: enhancement by interleukin 6 (IL–6) and inhibition by antibodies directed against Il–6 or its receptor. *J. Exp. Med.* 172:997–1000 The Rockefeller University Press (1990).

Ward, et al. High affinity interleukin–6 receptor is a hexameric complex consisting of two molecules each of interleukin–6, interleukin–6 receptor, and gp–130. *The Journal of Biological Chemistry* 269:23286–23289 The American Society for Biochemistry and Molecular Biology, Inc. U.S.A. (1994).

Yamasaki, et al. Cloning and expression of the human interleukin–6 (BSF–2/IFNB 2 ) receptor. *Science* 241:825–828 (1988).

D'Hellencourt, et al., "Immunomodulation by cytokine antisense oligonucleotides", European Cytokine Network, 6(1):7–19, (1995).

Keller, et al., "Effect of IL–6 receptor antisense oligodeoxynucleotide on in vitro proliferation of myeloma cells", J. Immunol., 154(8):4091–4098, (1995).

Reddy et al., "Interleukin–6 antisense deoxynucleotides inhibit bone resorption by giant cells from human giant cell tumors of bone", J. Bone Miner. Res., 9(5):753–757, (1994).

Miller, et al., "Gene Transfer and Antisense Nucleic Acid Techniques", Parasitiology Today, 10(3):92–97, (Mar. 1994).

Stein, et al., "Antisense Oligonucleotides as Therapeutic Agents–Is the Bullet Really Magical", Science, 261:1004–1012, (Aug. 20, 1993).

Wu–Pong, S., "Oligonucleotides: Opportunities for Drug Therapy and Research", Pharmaceutical Technology, 18:102–114, (Oct. 1994).

Wagner, R., Gene inhibition using antisense oligodeoxynucleotides, Nature, 372:333–335, (Nov. 1994).

Weiss, R., "Upping the Antisense Ante", Science News, 139:108–109, (Feb. 16, 1991).

Bennett, F., "Antisense Research", Science, 271:434, (Jan. 26, 1996).

Uhlmann, et al., Antisense Oligonucleotides: A New Therapeutic Principle, Chemical Reviews, 90(4):543–584, (Jun. 1990).

Gewirtz et al., "Facilitating oligonucleotide delivery: Helping antisense deliver on its promise." *Proc. Natl. Acad. Sci. USA* 93:3161–3163 (1996).

Gura, T., "Antisense Has Growing Pains." *Science* 270:575–577 (1995).

Keller et al., "Effect of IL–6 Receptor Antisense Oligodeoxynucleotide on In Vitro Proliferation of Myeloma Cells." *J. Immunol.* 154:4091–4098 (1995).

Milligan et al., "Current Consepts in Antisense Drug Design." *Journal of Medical Chemistry* 36(14):1923–1937 (1993).

Plenat, F., "Animal models of antisense oligonucleotides: lessons for use in humans." *Molecular Medicine Today* 2(6):250–257 (1996).

Rojanasakul, Y., "Antisense oligonucleotide therapeutics: drug delivery and targeting." Advanced Drug Design Reviews 18:115–131 (1996).

Stull et al., "Antigene, Ribozyme and Aptamer Nucleic Acid Drugs: Progress and Prospects." *Pharmaceutical Research* 12(4):465–483 (1995).

Zon et al., "Phosphorothioate oligonucleotides", Chapter Four in *Oligonucleotides and Analogues: A Practical Approach*, Eckstein, ed. IRL Press, pp. 87–108 (1991).

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (xi) SEQUENCE DESCRIPTION: SEQ ID NO:1:

CGGCTGCAGG CTCCCACCCC AGCAGATGGG CTGGCATGGG AAGGAGGCTG      50

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

CCACAGCGCC GCACCTGAGC      20

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (xi) SEQUENCE DESCRIPTION: SEQ ID NO:3:

GAAAACATTT GAGGAACTC      19

(2) INFORMATION FOR SEQ ID NO:4:

(i) SEQUENCE CHARACTERISTICS:

(A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

ACACTGCGAG TCCCTCG                                                          17

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:5:

GCGGACTGGC TAATGGGAA                                                        19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:6:

GAGTCGTGGA GCTGCACCGA                                                       20

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:7:

GCTCCGAGGA CCCCACTCA                                                        19

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

CGGGACTGCT AACTGGCA                                                         18

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

GCTCCCGACA CTACTGGCGA C                                                     21

(2) INFORMATION FOR SEQ ID NO:10:

(i) SEQUENCE CHARACTERISTICS:
        (A) LENGTH: 17 base pairs
        (B) TYPE: nucleic acid

```
        (C) STRANDEDNESS: single
        (D) TOPOLOGY: linear (xi) SEQUENCE DESCRIPTION: SEQ ID NO:10:

GGTGGACACC TCGTTCT                                                    17

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

TTTCCCCTGG CGTAGAACCT                                                 20

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:12:

GGGCAGCCAG CAGCGCGCA                                                  19

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

AGCTGCACCG ACCTCAGCAG CAG                                             23

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

CCTGCTGCCG GCTTCCTGAG                                                 20

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:15:

TCTGCTGGGG TGGGAGCCTG CA                                              22

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(xi) SEQUENCE DESCRIPTION: SEQ ID NO:16:

CCCATGCCAG CCCATCTCCT                                                    20

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:17:

GCGGACAGGC TAATGGGAA                                                     19

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

CCTGCAGCCG GCTTCCTGAG                                                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

CCCATGCCAG CCCATCTGCT                                                    20

OLIGONUCLEOTIDES AND METHODS FOR INHIBITING CELLULAR PROLIFERATION

This application is a continuation of application Ser. No. 08/486,408 filed Jun. 7, 1995, now U.S. Pat. No. 5,716,846.

FIELD OF THE INVENTION

The present invention relates to methods for treating disease using oligonucleotides which are effective inhibitors of cellular proliferation. In particular, it relates to methods for inhibiting disease-associated cellular proliferation using therapeutic agents comprising oligonucleotides which are substantially complementary to interleukin-6 receptor mRNA sequences.

BACKGROUND OF THE INVENTION

Cellular growth, function, differentiation and development are regulated by a variety of different mechanisms. Among the most important regulators of cells are the receptor-specific proteins called "cytokines". These proteins bind to specific membrane-associated receptors which, in turn, transduce intracellular signals that ulitmately regulate the expression of critical genes and thereby control many cellular functions.

Interleukin-6 ("IL-6") is one of the most well characterized and studied cytokines. It functions through the interaction with at least two transmembrane glyprotein receptor molecules on the surface of target cells (Taga, et al., J. Exp. Med. 166: 967–981 (1987); the interleukin-6 receptor ("IL-6R") and the signal transducer, gp130 (Yamasaki, et al., Science 241: 825–828 (1988); and Hibi et al., Cell 63: 1149–1157 (1990)). Signal transduction by IL-6 involves the concerted action of both IL-6R and gp130. Initially, IL-6 binds to IL-6R with low affinity (Taga et al., Cell 58: 573–581 (1989)). This initial binding event induces the formation of a ternary complex consisting of two molecules of gp130 dimerized with two IL-6/IL-6R ligand-receptor complexes. In this ternary complex, IL-6 is bound with high affinity resulting in the transduction of intracellular signals by the gp130 molecules (Ward et al., J. Biol. Chem. 269: 23286–23289 (1994)).

In addition to playing an important role in modulating normal cellular function, IL-6 overproduction has been implicated in many different disease states. Recently, many investigators have focused on the suppression of IL-6 production, function and/or signal transduction as potentially useful means of inhibiting the cellular proliferation which is associated with different disease states. Vink, et al. (J. Exp. Med. 1: 997–1000(1990)) describe the inhibition of plasmacytoma growth in vivo by using antibodies directed against IL-6 or its receptor component, IL-6R. More recently, antisense oligonucleotides have been studied for use as inhibitors of cellular proliferation. Levy et al. (J Clin. Invest. 88: 696–699 (1991)) describe the use of antisense oligonucleotides which are complementary to the mRNA encoding the IL-6 protein. Fujita (PCT Application No. WO 94/25036) describes the use of antisense oligonucleotides which are complementary to the initiator codon of the mRNA encoding IL-6R.

The field of "antisense therapeutics" refers to the use of oligonucleotides which are complementary to target nucleic acids, most usually mRNA, as regulators of nucleic acid function. An antisense oligonucleotide, i.e. an oligonucleotide having a nucleic acid sequence which is complementary to that of the "sense" nucleic acid to which it is targeted, can function in many different ways to modulate nucleic acid function. When the targeted nucleic acid is MRNA, it may function by preventing translation of the MRNA into protein or inhibiting the binding or translocation of ribosomes. When the targeted nucleic acid is DNA, it may prevent transcription into mRNA.

In addition to inhibiting the production and/or function of MRNA by a "sequence specific" antisense mechanism, the effect of certain oligonucleotides, and particularly phosphorothioate oligonucleotides, can be partially attributed to non-sequence specific mechanisms. Such mechanisms have been reported to account for some of the effects of phosphorothioate oligonucleotides as anti-viral agents. (Stein, et al., Pharmac. Ther. 52: 365–384 (1991); Majumdar, et al., Biochemistry 28: 1340 (1989)).

It is an object of the present invention to provide oligonucleotides which effectively inhibit disease-associated cellular proliferation and/or growth. Such oligonucleotides are complementary to the mRNA encoding the IL-6R, and function via sequence specific and/or non-sequence specific mechanisms. A further objective of the present invention is to provide pharmaceutical compositions suitable for administration to human subjects comprising these oligonucleotides.

SUMMARY OF THE INVENTION

The present invention features methods for inhibiting disease-associated cellular proliferation using therapeutic agents comprising oligonucleotides which are substantially complementary to interleukin-6 receptor MRNA sequences. The preferred uses of the methods described herein are in the treatment of a patient suffering from cancer, such as renal cell carcinoma, an autoimmune disease or a viral infection. Other uses of the present invention include detecting the presence of the interleukin-6 receptor mRNA by using the oligonucleotides as in vitro detection probes. These detection probes would be particularly useful in evaluating the effectiveness of other therapeutic agents in reducing interleukin-6 receptor mRNA levels.

The method of the present invention employs therapeutic agents composed of oligonucleotides which are specific for interleukin-6 receptor mRNA. The preferred oligonucleoitdes are based on the following sequences:

```
SEQ. ID. NO. 2     CCACAGCGCC GCACCTGAGC

SEQ. ID. NO. 3     GAAAACATTT GAGGAACTC

SEQ. ID. NO. 4     ACACTGCGAG TCCCTCG

SEQ. ID. NO. 5     GCGGACTGGC TAATGGGAA

SEQ. ID. NO. 6     GAGTCGTGGA GCTGCACCGA

SEQ. ID. NO. 7     GCTCCGAGGA CCCCACTCA

SEQ. ID. NO. 8     CGGGACTGCT AACTGGCA

SEQ. ID. NO. 9     GCTCCCGACA CTACTGGCGA C

SEQ. ID. NO. 10    GGTGGACACC TCGTTCT

SEQ. ID. NO. 11    TTTCCCCTGG CGTAGAACCT

SEQ. ID. NO. 12    GGGCAGCCAG CAGCGCGCA

SEQ. ID. NO. 13    AGCTGCACCG ACCTCAGCAG CAG

SEQ. ID. NO. 14    CCTGCTGCCG GCTTCCTGAG

SEQ. ID. NO. 15    TCTGCTGGGG TGGGAGCCTG CA
```

```
SEQ. ID. NO. 16    CCCATGCCAG CCCATCTCCT
```

Oligonucleotides having nucleic acid sequences substantially corresponding to a preferred nucleic acid sequence and consisting essentially of the preferred nucleic acid sequence (i.e. having a nucleic acid sequence which is substantially the same) are also covered by the present invention. In particular, nucleic acid sequences which substantially correspond to SEQ. ID. NO.s 5, 14 and 16 above, and are given by SEQ. ID. NO. 17, 18 and 19 as follows, respectively, are expressly covered by the present invention:

```
SEQ. ID. NO. 17    GCGGACAGGC TAATGGGAA

SEQ. ID. NO. 18    CCTGCAGCCG GCTTCCTGAG

SEQ. ID. NO. 19    CCCATGCCAG CCCATCTGCT
```

More particularly, the present invention features a method of inhibiting disease-associated cellular proliferation comprising the step of contacting the cells with a purified oligonucleotide 12 to 100 nucleotides in length, said oligonucleotide being substantially complementary to a nucleic acid sequence in the mRNA encoding the interleukin-6 receptor, wherein said oligonucleotide consists essentially of a nucleic acid sequence selected from the group consisting of:

```
SEQ. ID. NO. 2     CCACAGCGCC GCACCTGAGC

SEQ. ID. NO. 3     GAAAACATTT GAGGAACTC

SEQ. ID. NO. 4     ACACTGCGAG TCCCTCG

SEQ. ID. NO. 5     GCGGACTGGC TAATGGGAA

SEQ. ID. NO. 6     GAGTCGTGGA GCTGCACCGA

SEQ. ID. NO. 7     GCTCCGAGGA CCCCACTCA

SEQ. ID. NO. 8     CGGGACTGCT AACTGGCA

SEQ. ID. NO. 9     GCTCCCGACA CTACTGGCGA C

SEQ. ID. NO. 10    GGTGGACACC TCGTTCT

SEQ. ID. NO. 11    TTTCCCCTGG CGTAGAACCT

SEQ. ID. NO. 12    GGGCAGCCAG CAGCGCGCA

SEQ. ID. NO. 13    AGCTGCACCG ACCTCAGCAG CAG

SEQ. ID. NO. 14    CCTGCTGCCG GCTTCCTGAG

SEQ. ID. NO. 15    TCTGCTGGGG TGGGAGCCTG CA

SEQ. ID. NO. 16    CCCATGCCAG CCCATCTCCT

SEQ. ID. NO. 17    GCGGACAGGC TAATGGGAA

SEQ. ID. NO. 18    CCTGCAGCCG GCTTCCTGAG

SEQ. ID. NO. 19    CCCATGCCAG CCCATCTGCT
```

Yet another aspect of the present invention is a method of inhibiting disease-associated proliferation of cells comprising the step of contacting the cells with a purified oligonucleotide 12 to 100 nucleotides in length, said oligonucleotide being substantially complementary to a nucleic acid sequence region of 50 nucleotides present in the mRNA encoding IL-6R (abut having T substituted for U) consisting of:

```
SEQ. ID. NO. 1:
CGGCTGCAGG CTCCCACCCC AGCAGATGGG CTGGCATGGG

AAGGAGGCTG,
``` wherein said oligonucleotide inhibits proliferation of cells in vivo or in vitro.

Other features and advantages of the invention are apparent from the following detailed description and the claims.

DETAILED DESCRIPTION

The present invention concerns methods of using oligonucleotides which inhibit cellular proliferation. In order to more clearly describe the subject matter of the present invention, certain terms used herein shall be defined as follows unless otherwise indicated:

Antisense Oligonucleotide: "Antisense oligonucleotide" means an oligonucleotide which is complementary to a target "sense" nucleic acid, and functions at least partially by sequence-specific mechanisms to regulate the functioning of the target nucleic acid.

Complementary: "Complementary", when used to refer to a nucleic acid, means a nucleic acid of one polarity containing a sequence of nucleotides whose bases pair via Watson-Crick hydrogen bonds with the nucleotide bases of another nucleic acid of opposite polarity, i.e. adenine ("A") pairs with thymine ("T") or uracil ("U"), and guanine ("G") pairs with cytosine ("C"). For example, a nucleic acid having the sequence GCAU in the 5' to 3' direction is "complementary" to a nucleic acid having the sequence CGTA in the 3' to 5' direction. Use of the term complementary herein is intended to include those nucleic acids which are substantially complementary such that, despite occasional mismatches between the strands, a stable duplex will nevertheless be formed. The individual strands of a complementary nucleic acid pair can also be referred to as the plus ("(+)") or "sense" strand and the minus ("(-)") or "antisense" strand.

Disease-associated Cellular Proliferation: "Disease-associated cellular proliferation" means an abnormal level of cell division and/or growth which is caused by or associated with a particular disease such as cancer or viral infection.

Hybridize: "Hybridize" means the formation of a duplex between complementary nucleic acids via base pair interactions.

Liposome: "Liposome" means a vesicle composed of amphipathic lipids arranged in a spherical bilayer or bilayers.

Modified: "Modified", when used to refer to a nucleic acid, means a nucleic acid in which any of the natural structures have been altered. These include modifications to the phosphodiester linkages, the sugars (ribose in the case of RNA or deoxyribose in the case of DNA) and/or the purine or pyrimidine bases. Modified phosphodiester linkages include phosphorothioates, phosphotriesters, methylphosphonates and phosphorodithioates. "Modified dNTPs" refers to nucleoside triphosphates which, when incorporated into a nucleic acid, will result in the formation of modified nucleic acids.

Nucleic Acid Sequence: "Nucleic acid sequence", or "sequence", means both a nucleic acid having a particular sequence of nucleotides, and also the sequence or order of nucleotides present in a particular nucleic acid. Which of these two meanings applies will be apparent form the context in which this term is used.

Oligonucleotide: "Oligonucleotide" means an oligodeoxyribonucleotide having a defined nucleic acid sequence.

Pharmacologically compatible carrier: "Pharmacologically compatible carrier means a formulation to which the oligonucleotide can be added to facilitate its administration to a patient and/or efficacy without exhibiting any unacceptable levels of toxicity or pharmacologically adverse effects.

Phosphorothioate oligonucleotide: "Phosphorothioate oligonucleotide" means an oligonucleotide having all phosphorothioate linkages in place of naturally occurring phosphodiester linkages.

Phosphorothioate-containing oligonucleotide: "Phosphorothioate-containing oligonucleotide" means an oligonucleotide having at least one and as many as all phosphorothioate linkages. This term is intended to include phosphorothioate oligonucleotides.

Polarity: "Polarity" means the orientation of a nucleic acid polymer which is created when the C3 position of one deoxyribose (or ribose) moiety is linked together with the C5 of the adjacent deoxyribose (or ribose) moiety via a phosphate linkage. The polarity of nucleic acids is referred to as 5' to 3' or 3' to 5'.

Polymerase: "Polymerase" means an enzyme which is capable of catalyzing the sequential addition of nucleotides to a nucleic acid.

Primer: "Primer" means an oligonucleotide that is complementary to a template that hybridizes with the template to initiate synthesis by a polymerase, such as reverse transcriptase, and which is extended by the sequential addition of covalently bonded nucleotides linked to its 3' end that are complementary to the template.

Substantially Complementary: "Substantially Complementary", when used to refer to a nucleic acid, means having a sequence such that not all of the nucleotides exhibit base pairing with the nucleotides of another nucleic acid, but the two nucleic acids are nonetheless capable of forming a stable hybrid under appropriate conditions.

Template: "Template" means the nucleic acid having the sequence of nucleotides which will provide the pattern and serve as substrate for producing a desired oligonucleotide. In order to serve as such, the template must also contain a sequence which is capable of hybridizing with a primer or, in the case of self-priming templates, capable of forming a self-priming region.

Therapeutically effective amount: "Therapeutically effective amount" means an amount which is effective in inhibiting disease-associated cellular proliferation and/or growth in a patient suffering from a disease associated with overproduction of IL-6. Preferably, the therapeutically effective amount relieves, to some extent one or more symptoms associated with the disease.

The development of therapeutic applications using oligonucleotides is now widespread. Although the precise mechanism of action of oligonucleotides as therapeutic agents is often difficult to determine, many proposed mechanisms have been suggested and any or all of these different mechanisms may act in concert to produce a desired result. One mechanism of action is based on antisense. Antisense oligonucleotides are generally designed to have sequences which are complementary to specific sequences found in target nucleic acids such as DNA, mRNA or precursor mRNA. By hybridizing to a specific sequence in the target nucleic acid, the antisense oligonucleotide interrupts the protein-encoding function of the DNA.

Some of the proposed mechanisms which may account for the antisense function of a particular oligonucleotide may include: cleavage of RNA in a RNA:DNA hybrid by an enzyme having RNase H activity; premature termination of mRNA transcription; prevention of translocation of the mRNA to the site for protein translation; interference with mRNA processing by hybridizing to an mRNA intron/exon; interference with mRNA function by hybridizing to non-protein coding (untranslated) regions; and/or interference with ribosome binding by hybridizing to an mRNA initiator codon. In summary, each of these sequence-specific antisense mechanisms act in some way to inhibit the expression of a particular gene.

In addition to sequence-specific antisense mechanisms, certain modified oligonucleotides can inhibit nucleic acid function via a non-sequence specific mechanism. In some instances, when the effects of antisense oligonucleotides are compared to "control" oligonucleotides which contain the same bases in randomized order, the control oligonucleotides also exhibit inhibition of protein production. Although the precise mechanism for such non-sequence specific mechanisms is not known, these effects have been attributed to the accidental inhibition of other essential genes by the control oligonucleotides. (See Milligan, et al., in *Antisense Therapeutics;* Development of Antisense Therapeutics, Annals of the New York Academy of Sciences, p. 229–241.)

One potential explanation for non-sequence specific effects of oligonucleotides on proliferation of renal carcinoma cells is the inhibition of topoisomerase. Many anticancer agents with activity against renal cell carcinoma have been demonstrated to inhibit topoisomerase. (Shuin, et al., Anticancer Research 14: 2621–2626 (1994)). It is hypothesized that topoisomerase inhibition by phosphorothioate oligonucleotides may account for a portion of the observed antiproliferative effects attributable to the phosphorothioate oligonucleotide.

In any case, both sequence specific and non-sequence specific mechanisms may account for the effects of the oligonucleotides of the present invention. A complete understanding of the mechanisms of action is not necessary for the design of cellular function-inhibiting oligonucleotides.

The oligonucleotides of the present invention are complementary to the mRNA encoding the IL-6R protein, and may inhibit IL-6R production via antisense and/or other mechanisms. Therapeutic agents which inhibit the functioning of IL-6, such as those which regulate the production of IL-6R, can be used to counteract the effects of overproduction of IL-6. The normal functioning of IL-6 involves the induction of IL-6 production by many different cell types, such as fibroblasts, macrophages, endothelial cells and keratinocytes, as a response to injury or infection. In the absence of injury or infection, these cells do not normally produce IL-6. IL-6 production results in an enhancement of the immune response via a variety of mechanisms which include B- and T- cell proliferation or differentiation as well as T-cell and macrophage activation.

However, IL-6 overproduction is implicated in many different disease states. For example, IL-6 hyperexpression in Epstein Barr virus infected B lymphocytes has been shown to be partially responsible for tumorigenicity (Scala et al., J. Exp. Med. 17: 61–68 (1990)). The overproduction of IL-6 by keratinocytes has been shown to play a causative role in the epidermal hyperplasia associated with psoriasis (Grossman et al., Proc. Nat. Acad. Sci. 86: 6367–6371 (1989)). Overproduction of IL-6 by renal carcinoma cells has been shown to be associated with increased metastases (Takenawa, et al., Journal of the National Cancer Institute 83(22): 1668–1672(1991)). IL-6 also plays a reported role in the increase of bone resorption during menopause due to its enhancement of osteoclast development (Jilka et al., Science 257: 88–91 (1992); and Girasole et al., Journal of Clinical Investigation 89: 883–891(1992)). Additionally, IL-6 has been shown to be a tumor growth factor for multiple myeloma cells (Klein, et al., Eur. Cytokine Net., 1(4): 193–201(1990)). Other disease states which have been associated with IL-6 overproduction include plasma cell leukemia, cachexia, mesangial proliferative glomerulonephritis, Kaposi's sarcoma, rheumatoid arthritis, hypergammaglobulinemia, Castleman's disease, IgM gamopathy, cardiac myxoma and autoimmune insulin-dependent diabetes.

Thus, therapeutic agents which are designed to inhibit IL-6 function have a widespread therapeutic application. They can be used as a therapeutic agent in the treatment of any of the aforementioned disease states. The antisense oligonucleotides of the present invention are preferably used to treat renal cell carcinoma.

The oligonucleotides of the present invention can be either DNA or RNA, but are preferably DNA. The oligonucleotides can be prepared using any known chemical or enzymatic methods. Chemical synthesis can be conveniently performed according to the method described by Stec et al. (J. Am. Chem. Soc. 106: 6077–6079 (1984)) using the phosphoroamidite method and an automated synthesizer, such as Model 380-B (Applied Biosystems, Inc., Foster City, Calif.).

The oligonucleotides included within the present invention can be either unmodified or modified. Modified oligonucleotides can be prepared by altering any of the natural structures of a nucleic acid. These structures include the phosphodiester linkages, the sugars (ribose in the case of RNA or deoxyribose in the case of DNA) and/or the purine or pyrimidine bases. Any modification can be made to an oligonucleotide as long as it does not render the oligonucleotide ineffective at hybridizing to the target nucleic acid or toxic, if to be used in vivo. This includes certain modifications which may diminish hybridization efficiency without completely preventing the formation of a stable duplex.

Preferred modifications are to the phosphodiester linkages to render them more stable in the presence of nucleases. Modifying the phosphodiester linkages may also enhance cellular uptake. Modified phosphodiester linkages include phosphorothioate, methylphosphonate, phosphorodithioate, or phosphoselenate linkages. The oligonucleotides may contain all modified linkages, a mixture of different modified linkages, a mixture of modified linkages and unmodified linkages, or any combination of these which are either selectively positioned, or present in different regions of the oligonucleotide as in a chimeric oligonucleotide. Oligonucleotides with modified internucleotide linkages can be synthesized in the same manner as unmodified oligonucleotides by known methods, including many of the methods discussed above.

Other examples of modifications include the incorporation of modified sugar groups such as alpha-anomers or the sugars incorporated into 2'-O-methyloligonucleotides. Also contemplated are modifications to the nucleotide purine or pyrimidine bases.

Preferably, the oligonucleotides of the present invention contain phosphorothioate linkages which increase stability, facilitate cellular uptake and may enable the oligonucleotides to inhibit cellular functions by sequence independent mechanisms as well as sequence specific antisense mechanisms.

The antisense oligonucleotides of the present invention are preferably about 12 to 100 nucleotides in length. More preferably, these oligonucleotides are about 14 to 50 nucleotides in length, and most preferably about 18 to 35 nucleotides in length. Oligonucleotide length should be selected to optimize the efficiency of the oligonucleotide in inhibiting disease-associated cellular proliferation and/or growth. The existence of any modifications in the oligonucleotide will also influence the effects of length on overall efficiency of the oligonucleotide.

In order to determine the optimal oligonucleotide size, several factors should be taken into account. Oligonucleotides which are short have the advantage of being more easily internalized by cells. However, if they are not long enough, for example less than 10 bases, they may not form specific and stable hybrids with target sequence. On the other hand, longer oligonucleotides may hybridize to their targets with increased stability which may enhance translation arrest by preventing a ribosome from displacing the oligonucleotide. However, if the oligonucleotide is too long, for example greater than 150 bases, it may not be efficiently taken up by cells and/or could potentially be cytotoxic.

An oligonucleotide screening assay designed to mimic physiological conditions can be utilized to predict the efficiency with which the oligonucleotides hybridize in living cells. Such a screening assay is described by Nelson et al., in WO 95/03427.

The oligonucleotides of the present invention are specific for a particular target sequence. More particularly, this target sequence is the mRNA which encodes IL-6R and is described by Yamasaki, et al., Science 241: 825–828 (1988). By being "specific for", it is intended that the oligonucleotides are complementary to the target sequence. Preferably, the target sequence is an early protein coding region of the IL-6R mRNA given by SEQ. ID. NO. 1 as follows:

```
SEQ. ID. NO. 1:
CGGCTGCAGG CTCCCACCCC AGCAGATGGG CTGGCATGGG AAGGAGGCTG
```

Preferred oligonucleotides of the present invention are given by the following sequences:

```
SEQ. ID. NO. 2     CCACAGCGCC GCACCTGAGC

SEQ. ID. NO. 3     GAAAACATTT GAGGAACTC

SEQ. ID. NO. 4     ACACTGCGAG TCCCTCG

SEQ. ID. NO. 5     GCGGACTGGC TAATGGGAA

SEQ. ID. NO. 6     GAGTCGTGGA GCTGCACCGA

SEQ. ID. NO. 7     GCTCCGAGGA CCCCACTCA

SEQ. ID. NO. 8     CGGGACTGCT AACTGGCA

SEQ. ID. NO. 9     GCTCCCGACA CTACTGGCGA C

SEQ. ID. NO. 10    GGTGGACACC TCGTTCT

SEQ. ID. NO. 11    TTTCCCCTGG CGTAGAACCT

SEQ. ID. NO. 12    GGGCAGCCAG CAGCGCGCA
```

-continued

SEQ. ID. NO. 13    AGCTGCACCG ACCTCAGCAG CAG

SEQ. ID. NO. 14    CCTGCTGCCG GCTTCCTGAG

SEQ. ID. NO. 15    TCTGCTGGGG TGGGAGCCTG CA

SEQ. ID. NO. 16    CCCATGCCAG CCCATCTCCT

SEQ. ID. NO. 17    GCGGACAGGC TAATGGGAA

SEQ. ID. NO. 18    CCTGCAGCCG GCTTCCTGAG

SEQ. ID. NO. 19    CCCATGCCAG CCCATCTGCT

Particularly preferred sequences are given by SEQ. ID. NO.s 15 and 16.

It is not necessary for the entire oligonucleotide sequence to be perfectly complementary to the target IL-6R mRNA sequence. It is only necessary for the oligonucleotide to be "substantially complementary", i.e. capable of forming a stable hybrid with the target. Additional non-complementary nucleotides may be present in the antisense oligonucleotide at any location, for example at either the 3' or 5' terminus, or any other location therebetween. Such additional non-complementary nucleotides may serve to inhibit in-vivo degradation and/or enhance the effects of the oligonucleotide in interfering with gene expression. The amount of complementarity necessary to form a stable hybrid with the target sequence will depend on the types and amounts of modifications present, the types of bases involved in hydrogen bonding (e.g. G:C hydrogen bonding is stronger than A:T) and the length of the oligonucleotide.

In addition to their usefulness as therapeutic agents, the oligonucleotides described herein are also useful as diagnostic probes and as research tools, such as amplification primers. Utilizing labeled oligonucleotide probes which are specific for IL-6R mRNA, the presence or amount of IL-6R mRNA can be determined. The design and production of labeled oligonucleotide probes and their use in hybridization methods is easily accomplished by one of skill in the art.

Considerations for therapeutic use include oligonucleotide pharmacology and delivery. For use as therapeutic agents, the oligonucleotides must be pharmacologically suitable, i.e. they must exhibit minimal toxicity and suitable distribution and metabolism. Different pharmacological considerations can be evaluated using techniques which are known in the art.

Pharmaceutical compositions comprising the oligonucleotides in a pharmacologically acceptable carrier may be administered by a variety of different mechanisms which are well known to those of skill in the art. Such mechanisms include oral administration (inhalation or parenteral), injection (intravenous, intramuscular, subcutaneous, intraperitoneal), and topical administration (intranasally, cutaneous). Compositions which are suitable for each of these different mechanisms are routinely prepared and utilized.

Examples of pharmacologically acceptable carriers include aqueous solutions such as water, saline, buffers or carbohydrate solutions; and delivery vehicles such as liposomes, microspheres, or emulsions. Delivery vehicles can be utilized to enhance in vivo stability. Liposomes are preferred because of their ability to enhance intracellular delivery, their long circulation half-lifes, the ease of incorporation of receptor targeted molecules, their minimal toxicity and good biodegradability. Liposomes may be made by a variety of techniques known in the art. (See, for example, Bangham et al., J. Mol. Biol., 13: 238–252(1965)). These methods generally involve first dissolving and mixing the lipids in an organic solvent, followed by evaporation. Then an appropriate amount of the aqueous phase is mixed with the lipid phase, and then allowed to incubate for a sufficient time for the liposomes to form. The aqueous phase will generally consist of the biomolecule in suspension with other solutes, such as buffers or sugars.

The exact dosage and number of doses of the pharmaceutical compositions described herein depends upon several factors such as the disease indication, the route of administration, the delivery vehicle and the oligonucleotide composition. Duration of treatment will depend on the effects of the treatment on the disease symptoms, and may include multiple daily doses for extended periods of time.

EXAMPLE I

Synthesis of Oligoncleotides

Oligonucleotides containing phosphodiester linkages as well as modified linkages such as phosphorothioates can be synthesized by procedures well known in the art. For example, in Methods in Enzymology 154:287 (1987), Caruthers et al. describe a procedure for synthesizing oligonucleotides containing phosphodiester linkages by standard phosphoramidite solid-phase chemistry. Bhatt, U.S. Pat. No. 5,253,723, describes a procedure for synthesizing oligonucleotides containing phosphorothioate linkages. Klem et al., PCT WO92/07864 describe the synthesis of oligonucleotides having different linkages including methylphosphonate linkages.

Example II

Inhibition of Renal Cell Carcinoma Cellular Proliferation by Phosphorothioate Oligonucleotides In order to test the effectiveness of several different phosphorothioate oligonucleotides complementary to mRNA for IL-6R as inhibitors of cancer cell proliferation, two different cell lines were studied. Caki-1 cells (American Type Culture Collection, Rockville, Md.), a renal cell carcinoma derived cell line known to produce abnormally high levels of IL-6 were used, with 293 cells (American Type Culture Collection, Rockville, Md.), an EBV transformed normal renal cell line serving as the control.

Caki-1 or 293 cells were cultured in 48 well plates under conditions where the cells did not become confluent within the experimental time course. After the cells adhered to the plates (4–6 hours), cell culture medium containing the phosphorothioate oligonucleotides was added to the cultures, and medium alone was added to control cells. The cells were incubated under standard conditions (37° C., 5% $CO_2$), and on day 4 the medium was replaced. On day 7, the medium was removed and the cells released from the plates using trypsin. Cell numbers per well were determined by counting cell density using a hemocytometer. As shown in Table 2, 1 $\mu$M antisense oligonucleotides inhibited cell proliferation of Caki-1 cells by 70–90% but had little effect on the proliferation of control cells.

TABLE II

INHIBITION OF CELLULAR PROLIFERATION
BY PHOSPHOROTHIOATE OLIGONUCLEOTIDES

| Oligonucleotide | % Reduction of Caki-1 Cells |
|---|---|
| SEQ. ID. NO. 2 | 57 |
| SEQ. ID. NO. 3 | 38 |
| SEQ. ID. NO. 4 | 33 |
| SEQ. ID. NO. 5 | 45 |
| SEQ. ID. NO. 6 | 33 |
| SEQ. ID. NO. 7 | 42 |
| SEQ. ID. NO. 8 | 33 |
| SEQ. ID. NO. 9 | 52 |
| SEQ. ID. NO. 10 | 41 |
| SEQ. ID. NO. 11 | 35 |
| SEQ. ID. NO. 12 | 66 |
| SEQ. ID. NO. 13 | 43 |
| SEQ. ID. NO. 14 | 54 |
| SEQ. ID. NO. 15 | 92 |
| SEQ. ID. NO. 16 | 82 |

Example III

Inhibition of Multiple Myeloma Cell Proliferation by Phosphorothioate Oligonucleotides Cellular proliferation in the presence of a phosphqrothioate oligonucleotide given by SEQ. ID. NO. 15 was performed as described in Example II using two different multiple myeloma cell lines; U266 (American Type Culture Collection, Rockville, Md.) and RPMI (American Type Culture Collection, Rockville, Md.). Compared to the no-oligonucleotide control, there was a 34% and 20% reduction in cellular proliferation in U266 and RPMI cells, respectively.

Although the invention is described in terms of specific embodiments, many modifications and variations of the present invention are possible in light of the teachings. It is, therefore, to be understood that within the scope of the appended claims the invention may be practiced otherwise than as specifically described.

We claim:

1. An oligonucleotide up to 35 nucleotide bases in length and comprising at least 18 contiguous nucleotide bases which are perfectly complementary to a nucleotide base sequence region contained in a nucleic acid sequence consisting of:

SEQ ID NO. 1    CGGCTGCAGG CTCCCACCCC AGCAGATGGG

CTGGCATGGG AAGGAGGCTG.

2. An oligonucleotide up to 35 nucleotide bases in length and comprising a nucleotide base sequence selected from the group consisting of:

SEQ. ID. NO. 2     CCACAGCGCC GCACCTGAGC,

SEQ. ID. NO. 3     GAAAACATTT GAGGAACTC,

SEQ. ID. NO. 4     ACACTGCGAG TCCCTCG,

SEQ. ID. NO. 5     GCGGACTGGC TAATGGGAA,

SEQ. ID. NO. 6     GAGTCGTGGA GCTGCACCGA,

SEQ. ID. NO. 7     GCTCCGAGGA CCCCACTCA,

SEQ. ID. NO. 8     CGGGACTGCT AACTGGCA,

SEQ. ID. NO. 9     GCTCCCGACA CTACTGGCGA C,

SEQ. ID. NO. 10    GGTGGACACC TCGTTCT,

SEQ. ID. NO. 11    TTTCCCCTGG CGTAGAACCT,

SEQ. ID. NO. 12    GGGCAGCCAG CAGCGCGCA,

SEQ. ID. NO. 13    AGCTGCACCG ACCTCAGCAG CAG,

SEQ. ID. NO. 14    CCTGCTGCCG GCTTCCTGAG,

SEQ.ID.NO.15       TCTGCTGGGG TGGGAGCCTG CA,

SEQ.ID.NO.16       CCCATGCCAG CCCATCTCCT,

SEQ. ID. NO. 17    GCGGACAGGC TAATGGGAA,

SEQ. ID. NO. 18    CCTGCAGCCG GCTTCCTGAG, and

SEQ. ID. NO. 19    CCCATGCCAG CCCATCTGCT.

3. The oligonucleotide of claim 1 or 2, wherein said oligonucleotide contains one or more modified sugars, one or more modified internucleoside linkages, or one or more modified sugars and one or more modified internucleoside linkages.

4. The oligonucleotide of claim 3, wherein said modified internucleoside linkages are selected from the group consisting of phosphorothioate, methylphosphonate, phosphotriester, phosphorodithioate and phosphoselenate linkages.

5. The oligonucleotide of claim 4, wherein said modified internucleoside linkages are phosphorothioate linkages.

6. The oligonucleotide of claim 1 or 2, wherein said oligonucleotide is a phosphorothioate oligonucleotide.

7. The oligonucleotide of claim 2, wherein said oligonucleotide consists of:

SEQ. ID. NO. 2  CCACAGCGCC GCACCTGAGC.

8. The oligonucleotide of claim 2, wherein said oligonucleotide consists of:

SEQ. ID. NO. 3  GAAAACATTT GAGGAACTC.

9. The oligonucleotide of claim 2, wherein said oligonucleotide consists of:

SEQ. ID. NO. 4  ACACTGCGAG TCCCTCG.

10. The oligonucleotide of claim 2, wherein said oligonucleotide consists of:

SEQ. ID. NO. 5  GCGGACTGGC TAATGGGAA.

11. The oligonucleotide of claim 2, wherein said oligonucleotide consists of:

SEQ. ID. NO. 6  GAGTCGTGGA GCTGCACCGA.

12. The oligonucleotide of claim 2, wherein said oligonucleotide consists of:

SEQ. ID. NO. 7  GCTCCGAGGA CCCCACTCA.

13. The oligonucleotide of claim 2, wherein said oligonucleotide consists of:

SEQ. ID. NO. 8  CGGGACTGCT AACTGGCA.

14. The oligonucleotide of claim 2, wherein said oligonucleotide consists of:

SEQ. ID. NO. 9  GCTCCCGACA CTACTGGCGA C.

15. The oligonucleotide of claim 2, wherein said oligonucleotide consists of:

SEQ. ID. NO. 10  GGTGGACACC TCGTTCT.

16. The oligonucleotide of claim 2, wherein said oligonucleotide consists of:

SEQ. ID. NO. 11  TTTCCCCTGG CGTAGAACCT.

17. The oligonucleotide of claim 2, wherein said oligonucleotide consists of:

SEQ. ID. NO. 12  GGGCAGCCAG CAGCGCGCA.

18. The oligonucleotide of claim 2, wherein said oligonucleotide consists of:

SEQ. ID. NO. 13  AGCTGCACCG ACCTCAGCAG CAG.

19. The oligonucleotide of claim 2, wherein said oligonucleotide consists of:

SEQ. ID. NO. 14  CCTGCTGCCG GCTTCCTGAG.

20. The oligonucleotide of claim 2, wherein said oligonucleotide consists of:

SEQ. ID. NO. 17  GCGGACAGGC TAATGGGAA.

21. The oligonucleotide of claim 2, wherein said oligonucleotide consists of:

SEQ. ID. NO. 18  CCTGCAGCCG GCTTCCTGAG.

22. The oligonucleotide of claim 2, wherein said oligonucleotide consists of:

SEQ. ID. NO. 19  CCCATGCCAG CCCATCTGCT.

23. A method for inhibiting cytokine-induced cellular proliferation of a cell in culture, said method comprising the steps of:
a) providing an oligonucleotide up to 35 nucleotide bases in length and comprising at least 18 contiguous nucleotide bases which are perfectly complementary to a nucleotide base sequence region contained in a nucleic acid sequence consisting of:

SEQ ID NO. 1  CGGCTGCAGG CTCCCACCCC AGCAGATGGG

CTGGCATGGG AAGGAGGCTG; and b) contacting said cell with said oligonucleotide under conditions such that said oligonucleotide is delivered within said cell and hybridizes with said nucleotide base sequence region, thereby inhibiting cytokine-induced cellular proliferation of said cell.

24. A method for inhibiting cytokine-induced cellular proliferation of a cell in culture, said method comprising the steps of:
a) providing an oligonucleotide up to 35 nucleotide bases in and comprising a nucleotide base sequence selected from the group consisting of:

SEQ. ID. NO. 2   CCACAGCGCC GCACCTGAGC,

SEQ. ID. NO. 3   GAAAACATTT GAGGAACTC,

SEQ. ID. NO. 4   ACACTGCGAG TCCCTCG,

SEQ. ID. NO. 5   GCGGACTGGC TAATGGGAA,

SEQ. ID. NO. 6   GAGTCGTGGA GCTGCACCGA,

SEQ. ID. NO. 7   GCTCCGAGGA CCCCACTCA,

SEQ. ID. NO. 8   CGGGACTGCT AACTGGCA,

SEQ. ID. NO. 9   GCTCCCGACA CTACTGGCGA C,

SEQ. ID. NO. 10  GGTGGACACC TCGTTCT,

SEQ. ID. NO. 11  TTTCCCCTGG CGTAGAACCT,

SEQ. ID. NO. 12  GGGCAGCCAG CAGCGCGCA,

SEQ. ID. NO. 13  AGCTGCACCG ACCTCAGCAG CAG,

SEQ. ID. NO. 14  CCTGCTGCCG GCTTCCTGAG,

SEQ.ID.NO.15    TCTGCTGGGG TGGGAGCCTG CA,

SEQ.ID.NO.16    CCCATGCCAG CCCATCTCCT,

SEQ. ID. NO. 17  GCGGACAGGC TAATGGGAA,

SEQ. ID. NO. 18  CCTGCAGCCG GCTTCCTGAG, and

SEQ. ID. NO. 19  CCCATGCCAG CCCATCTGCT; and b) contacting said cell with said oligonucleotide under conditions such that said oligonucleotide is delivered within said cell and hybridizes with a nucleic acid sequence encoding the IL-6 receptor of said cell, so that cytokine-induced cellular proliferation of said cell is inhibited.

25. The method of claim 23 or 24, wherein said oligonucleotide contains one or more modified sugars, one or more modified internucleoside linkages, or one or more modified sugars and one or more modified internucleoside linkages.

26. The method of claim 25, wherein said modified internucleoside linkages are selected from the group consisting of phosphorothioate, methylphosphonate, phosphotriester, phosphorodithioate and phosphoselenate linkages.

27. The method of claim 23, wherein said modified internucleoside linkages are phosphorothioate linkages.

28. The method of claim 24 or 26, wherein said oligonucleotide is a phosphorothioate oligonucleotide.

29. The method of claim 24, wherein said oligonucleotide consists of:

SEQ. ID. NO. 2  CCACAGCGCC GCACCTGAGC.

30. The method of claim 24, wherein said oligonucleotide consists of:

SEQ. ID. NO. 3  GAAAACATTT GAGGAACTC.

31. The method of claim 24, wherein said oligonucleotide consists of:

SEQ. ID. NO. 4  ACACTGCGAG TCCCTCG.

32. The method of claim 24, wherein said oligonucleotide consists of:

SEQ. ID. NO. 5  GCGGACTGGC TAATGGGAA.

33. The method of claim 24, wherein said oligonucleotide consists of:

SEQ. ID. NO. 6  GAGTCGTGGA GCTGCACCGA.

34. The method of claim 24, wherein said oligonucleotide consists of:

SEQ. ID. NO. 7  GCTCCGAGGA CCCCACTCA.

35. The method of claim 24, wherein said oligonucleotide consists of:

SEQ. ID. NO. 8  CGGGACTGCT AACTGGCA.

36. The method of claim 24, wherein said oligonucleotide consists of:

SEQ. ID. NO. 9  GCTCCCGACA CTACTGGCGA C.

37. The method of claim 24, wherein said oligonucleotide consists of:

SEQ. ID. NO. 10  GGTGGACACC TCGTTCT.

38. The method of claim 24, wherein said oligonucleotide consists of:

SEQ. ID. NO. 11  TTTCCCCTGG CGTAGAACCT.

39. The method of claim 24, wherein said oligonucleotide consists of:

SEQ. ID. NO. 12  GGGCAGCCAG CAGCGCGCA.

40. The method of claim 24, wherein said oligonucleotide consists of:

SEQ. ID. NO. 13  AGCTGCACCG ACCTCAGCAG CAG.

41. The method of claim 24, wherein said oligonucleotide consists of:

SEQ. ID. NO. 14  CCTGCTGCCG GCTTCCTGAG.

42. The method of claim 24, wherein said oligonucleotide consists of:

SEQ. ID. NO. 17  GCGGACAGGC TAATGGGAA.

43. The method of claim 24, wherein said oligonucleotide consists of:

SEQ. ID. NO. 18  CCTGCAGCCG GCTTCCTGAG.

44. The method of claim 24, wherein said oligonucleotide consists of:

SEQ. ID. NO. 19  CCCATGCCAG CCCATCTGCT.

* * * * *